(12) United States Patent
Bisping

(10) Patent No.: US 6,708,067 B1
(45) Date of Patent: Mar. 16, 2004

(54) TEST CABLE ARRANGEMENT

(76) Inventor: Hans Jurgen Bisping, Am Lutterbuschgen 12, 52072 Aachen (DE)

( * ) Notice: Subject to any disclaimer, the term of this patent is extended or adjusted under 35 U.S.C. 154(b) by 0 days.

(21) Appl. No.: 09/623,359

(22) PCT Filed: Mar. 5, 1999

(86) PCT No.: PCT/EP99/01441
§ 371 (c)(1),
(2), (4) Date: Sep. 9, 2000

(87) PCT Pub. No.: WO99/46000
PCT Pub. Date: Sep. 16, 1999

(30) Foreign Application Priority Data

Mar. 10, 1998 (DE) .......................... 198 10 262

(51) Int. Cl.[7] ................................................. A61N 1/04
(52) U.S. Cl. ..................................................... 607/119
(58) Field of Search ....................... 607/1–76, 115–156; 600/372–396; 439/909

(56) References Cited

U.S. PATENT DOCUMENTS

| 4,141,367 A | 2/1979 | Ferreira | 128/419 PT |
| 5,411,539 A | 5/1995 | Neisz | 607/36 |
| 5,702,423 A * | 12/1997 | Hujimaki | 607/2 |
| 6,038,481 A * | 3/2000 | Werner et al. | 607/119 |

FOREIGN PATENT DOCUMENTS

DE          90 03 222          6/1990

* cited by examiner

Primary Examiner—George R. Evanisko
(74) Attorney, Agent, or Firm—Charles L. Schwab; Nexsen Pruet Jacobs Pollard, LLC

(57) ABSTRACT

The invention relates to a test cable which has an at least two-wire design and which is provided for a sterile application, e.g. during the implantation of a cardiac pacemaker. The test cable serves as an electrical connection between the probe (electrode connector 1) and the test device (24). The test cable comprises electrical connecting elements assigned to the test device (24) and the contact elements which can be connected to the electrical contact surfaces (contact pin 3 and electrode connector ring 4) of the probe. The test cable has a thin flexible litz wire line (12) and is designed as a disposable part. In addition, the first contact element is configured as an alligator clip (9) and the second contact element is configured or as a contact spring (5) or a contact sleeve.

14 Claims, 2 Drawing Sheets

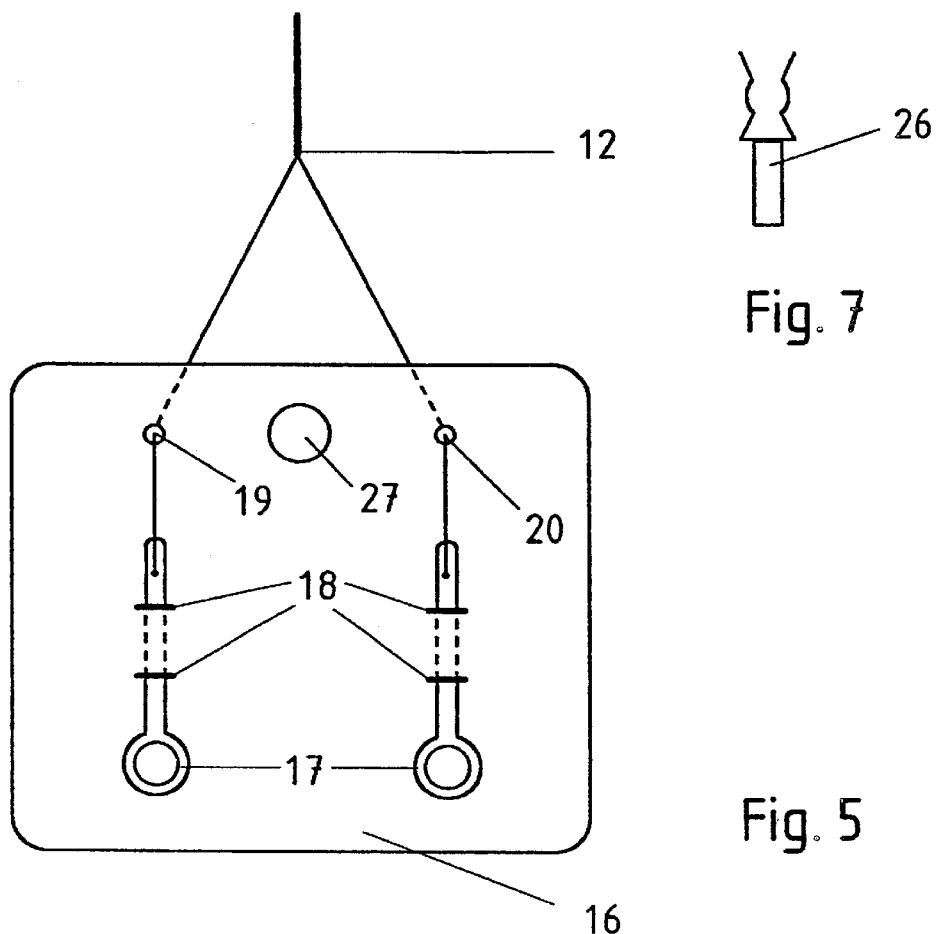
Fig. 7
Fig. 5
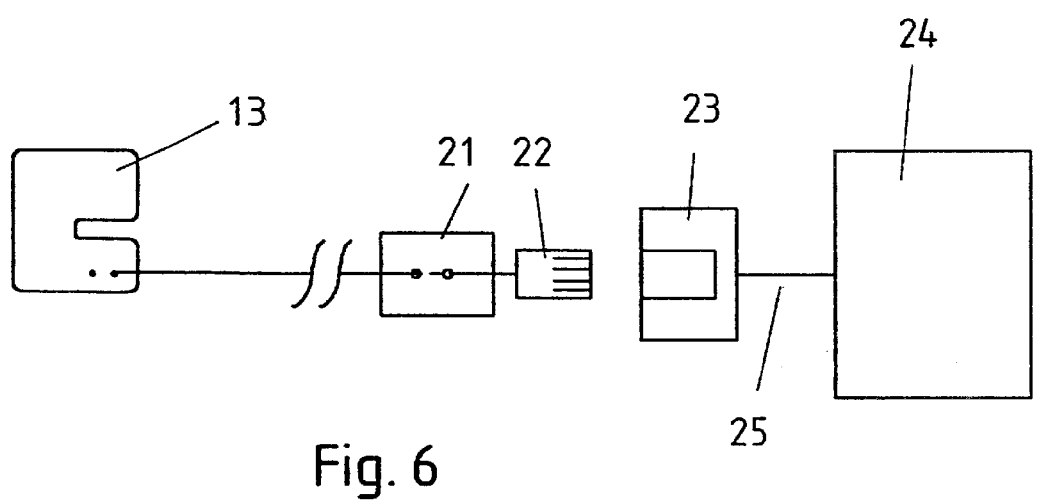
Fig. 6

TEST CABLE ARRANGEMENT

TECHNICAL FIELD

This invention relates to a test cable arrangement such as is used in the determination of electrophysiological parameters, for example in electrotherapy and electrodiagnostics.

BACKGROUND ART

In the implantation of heart pacemakers, defibrillators, neurostimulators and similar implants or in electrophysiological examination, the necessary electrodes or probes are usually initially introduced into the vascular system. As described in U.S. Pat. No. 4,141,367, issued Feb. 27, 1979 to L. A. Ferreira for a Cardiac Electrode/Pacer System Analyer, with the help of a suitable test cable, a connection is made between the sterile probe on the one hand and, on the other, the test instrument, which is located in the nonsterile zone. A sterile test cable arrangement is used for this purpose.

The resterilizable test cable used in this case is massively constructed and fitted with sturdy terminals. Their weight is correspondingly heavy and their flexibility correspondingly slight. These properties mean that the test cable cannot remain hooked up during the manipulation of the probe. Further, it is difficult to attach the alligator clips to the small plug of the probe in such a way that an adequately reliable connection is made without electrical contact errors occurring.

After the measurements have been performed, the measurement cable is then cleaned, dried, inspected for electrical and mechanical integrity, packaged, and finally subjected to sterilization. Aside from the logistical problem of having a sterile cable available at the proper time, another problem arises:

Because the cable is commonly inspected by care personnel without appropriate instructions and test apparatus, there is scarcely any assurance of quality control. Cable breaks, defects in insulation, intermittent contacts, or hygienic defects can result.

OBJECTS AND SUMMARY OF THE INVENTION

It is an object of the invention to furnish a test cable arrangement that avoids the stated disadvantages and to design a test cable that provides the needed consistent quality, sterility and continuous availability with simple resources. Good contact with the plug of the sonde must be guaranteed, and the test cable must be easy to use.

At the probe end, that is, in the sterile zone, the test cable has a support element with contact elements arranged thereon, the support element preferably being a paperboard card measuring approximately 6 cm×8 cm. Fastened to this paperboard is a tube-shaped contact spring with a hole into which the contact pin of an electrode plug fabricated in compliance with EN 50077—commonly called an IS-1 plug—is inserted.

In order to guarantee reliable electrical and mechanical contact, the contact spring is equipped with elastic elements or, as in the present case, exhibits a mechanical prestressing of the slotted tube.

The second electrical connection to the IS-1 electrode plug ring required for the measurement procedure in the case of bipolar probes is effected with an alligator clip. Contact spring and alligator clip are each connected to a thin twin-conductor wire, for example LIY (Z) with a wire cross-sectional area of 0.08 mm$^2$ and an outside diameter of 0.9 mm per strand.

In a further advantageous development of the invention, a support element is equipped with a contact terminal with axial access and a clamp terminal, the clamp terminal being arranged in the area of the electrode plug ring.

It is also possible to effect electrical contact with the contact surfaces of the probe not via a contact spring with axial access or an alligator clip, but by inserting the electrode plug on two clamp terminals. Such clamp terminals are known as holders for fine fuses, in which case the fuses are pressed into the clamp terminals. Arbitrary combinations of clamp terminals, contact springs and alligator clips are conceivable for the contacting of the probe connections.

The support element further has, on at least one external edge, guiding grooves or notches, which prevent the wire slipping off when it is wrapped around the support element in the storage or shipping condition.

At an appropriate place, the contact spring is soldered or otherwise electrically effectively connected, for example by crimping, to one strand of the wire. The other strand of the twin-conductor wire is electrically connected to the alligator clip or clamp terminal.

By way of tension relief, the twin-conductor wire, either as individual strands or as the whole, is passed through cutouts in the support element.

The length of the free strand of the twin-conductor wire connected to the alligator clip is a few centimeters longer than that of the strand connected to the contact spring. In this way, the alligator clip has enough room to move for clamping to the IS-1 connection.

If the probe system to be tested is a so-called unipolar configuration, the alligator clip is simply pulled off the support element, the free length of this wire strand is extended by separating the twin connection to the requisite length, and the alligator clip is brought into electrical contact with the tissue in known fashion.

The support element is made of a material, for example paperboard, the nature of which is such that it can be used only once. Cleaning by washing followed by resterilization is not possible with paperboard or cardboard. In this way, the entire test cable cannot be reused, and thus a new, quality-controlled test cable system must be employed for each measurement procedure.

It is easy to understand that single-use test cables according to the invention are ultimately more economical through mass production if the costs of cleaning, packaging and resterilization of conventional measurement cables as heretofore used, with all their time and personnel expense, are taken into consideration.

The other, proximal end of the electrical line in the form of the twin-conductor wire generally lies in the nonsterile zone and must finally be connected to the test apparatus.

This cable terminal must satisfy the following requirements: reliable electrical contact with the test apparatus and protection of the patient against dangerous voltages or currents.

The following solutions are proposed according to the invention:

The twin-conductor wire is attached to a second proximal support element made of, for example, paperboard, and its electrical conductors are connected to soldering eyes, which are arranged at separate locations, but at the edge of the support element if possible. Also provided for in this case are riveted, cemented, or the insertion connections already described above.

For contacting with the test instrument, the original connecting cable of the test instrument is now used, which cable does not need to be sterile in this case and therefore need not be subjected to the burdensome cleaning/sterilization procedure.

Because these test cables are as a rule equipped with two alligator clips, the rings of the soldering eyes readily suggest themselves as point of attachment.

It would also be conceivable, instead of the soldering eyes at the end of each strand of wire, to bend the stripped wire ends into loops and solder them together. The alligator clips of the measurement cable could then engage in these wire loops. The above-mentioned eyes or wire loops are to prevent the alligator clip from slipping off the wire strand.

Another alternative for the contacting of the wire to the test instrument is simply to separate the conductors of the wire and leave their ends insulated. The necessary electrical contact is achieved only when the ends are inserted into appropriate terminals and contact blades cut through the insulation. Such contactings are common, for example, in the case of RJ11 plugs, the so-called Western plugs from telephone technology.

It is further proposed that a plug connection, for example in the form of an RJ11-4 plug, be arranged at the proximal end of the wire, which preferably has a strand diameter of less than 0.95 mm, which plug connection is inserted into a mating socket of the test instrument or of a connecting cable. In order that test instruments already in service need not be modified, it is proposed that the alligator clips of the original test cable belonging to the test instrument be replaced with a mating socket at the patient end, that is, where the alligator clips are arranged. These RJ11 plug connections, known as Western plugs from telephone technology, have the following advantages: They are economical, are easy to connect to the wire, and have a safeguard against touching. If RJ11-4 plugs are used, they cannot be inserted in telephone jacks because they are designed for the receiver connection.

For better distinction, the twin-conductor wire should have wire strands in unlike colors.

The hole in the support element according to FIG. 2 serves to guide the probe. Specifically, if the probe is first inserted through this electrode hole from below and the IS1 contact pin is then connected to the contact spring, the IS-1 connection is fixed in the axis AA.

Also punched through the proximal support plate is a hole approximately 5 mm in size, which, however, serves in this case to fix in place the support plate, for example with the aid of a fabric clip, in order to prevent its slipping off when the cable of the test instrument is connected.

Another feature is the light weight and great flexibility of the arrangement. In the arrangement according to the invention, the mass of the wires is just roughly of the order of some 3 g/m (twin-conductor wire) for a strand diameter of approximately 0.9 mm. The mass of a 100 cm long test cable arrangement with proximal support element is only some 9 g. Because this thin, light and flexible wire requires the slightest flexural and torsional forces and thus poses scarcely any obstacle, the contactings can be left in place throughout the probe placement procedure.

Because the test cable is fabricated from fine-stranded, light and flexible wire and is made as a disposable part, quality and sterility are permanently assured.

If the wires are soldered to the alligator clips or contact springs and so forth, pointed and sharp edges cannot be prevented from occurring at the solder joints, which edges can under certain circumstances damage an OP glove. It is therefore proposed that adhesive dots made of paper or other material be affixed over the solder joints.

It is also proposed that the solder joints be arranged on the side facing the support element.

It is further proposed that the proximal support element have two electrically isolated contact surfaces, for example in the form of copper coatings on a plastic board, which are electrically connected to the respective wire strands. This contact card, which is about the size of a check card or smaller, is then inserted into a slot in the test instrument or a connected adapter and connects the wires to the test instrument.

If so-called two-chamber pacemakers are used, two electrodes are implanted, one in the atrium and one in the ventricle.

Suitable test instruments then have one connection both for the atrial and for the ventricular electrode. Accordingly, two separate measurement cables are also required.

For this application it is proposed that, for example, a Western plug (also known as an RJ11/RJ12/RJ45 modular plug) be connected to two twin-conductor wires, each of which has at its distal end a support element with the requisite contacting devices according to the configuration already described above and bears appropriate distinguishing features for use on the atrial and ventricular electrode, respectively.

It is further proposed that the contact layout of the modular connecting plug 22 in this case be such that a test cable arrangement according to the invention can be connected to a two-chamber test instrument via connecting socket 23 both for single-chamber application and for two-chamber application.

An arrangement is conceivable in which, for example, the twin-conductor wire for the atrial electrode is connected to contacts 1 and 2, which lie next to each other, and the twin-conductor wire for the ventricular electrode is connected to contacts 3 and 4.

A test cable according to the invention for a single-chamber application in the ventricle would then have only the contact layout 3 and 4.

BRIEF DESCRIPTION OF THE DRAWINGS

Further advantageous development of the invention can be inferred from the description of the drawings, in which the exemplary embodiments of the invention are described in greater detail.

FIG. 5 shows a view of a proximal support element.

FIG. 6 shows a schematic diagram of a test cable arrangement in which the proximal connection is made as a plug.

FIG. 7 shows a side view of a clamp terminal.

DETAILED DESCRIPTION OF THE INVENTION

Figure 1:
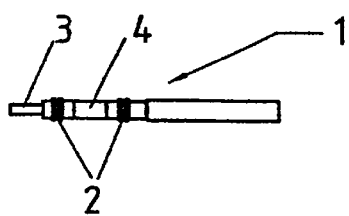
FIG. 1 shows a longitudinal view of an IS-1 connecting plug.
Figure 4:
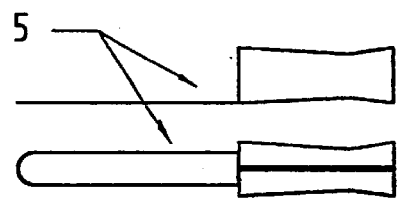
FIG. 4 shows a top and side view of a contact spring.

FIG. 1 shows an electrode plug 1 complying with the so-called IS-1 standard, which plug was introduced years ago in pacemaker and defibrillator therapy. The reference numeral 3 identifies the front contact pin of the IS-1 plug, and 4 identifies the back electrode plug ring. Seal rings 2 are made of insulating silicone rubber or polyurethane (PU) and delimit the region of electrode plug ring 4.

Figure 2:
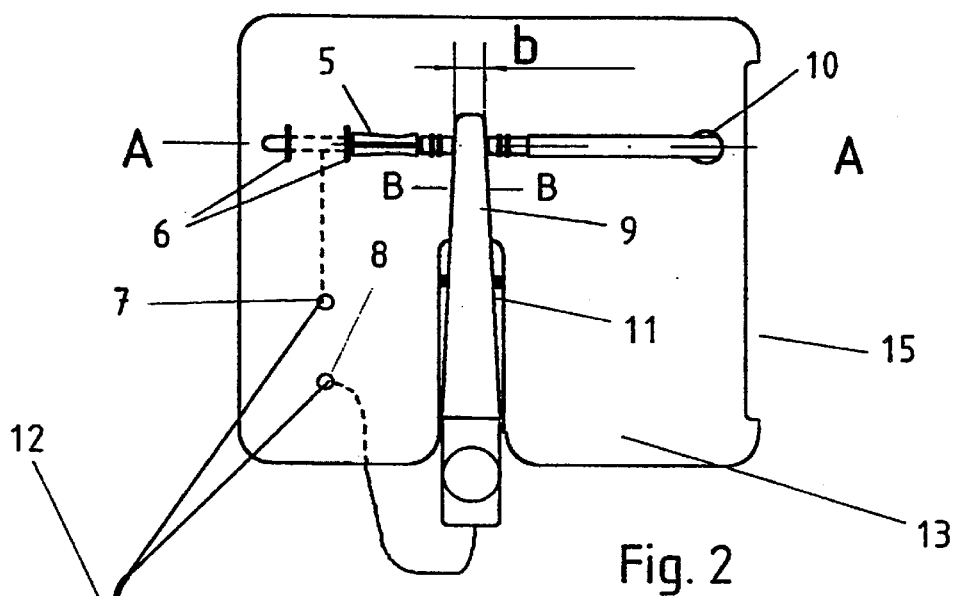
FIG. 2 shows a view of a support element.

FIG. 2 shows, approximately to scale, the part of the test cable arrangement that lies in the sterile zone and effects the electrical contact with the probe or electrode.

The probe with its plug 1 was first stuck from below through a hole 10, approximately 5 mm in size, in support element 13, and then contact pin 3 was inserted into the tubular hole in contact spring 5. The alligator clip 9 has a pair of pivotally connected jaws which are spring biased to a closed position.

In the storage and shipping phase, alligator clip 9 is arranged in guiding channel 11 in such a way that the front end of its gripping jaws end on line BB and fix the alligator clip in support element 13. After the attachment of IS-1 plug 1, as mentioned above, the jaws of the alligator clip 9 are manually opened and then placed so that the gripping jaws come to lie exactly over electrode ring 4 and one jaw makes electrical contact with electrode ring 4. The geometrical arrangement, above all of the guiding channel 11, is chosen such that the contacting jaw of alligator clip 9 comes to lie exactly over electrode plug ring 4 and not on one or more seal rings 2.

Guiding channel 11 thus limits the mobility of alligator clip 9 not only in the lateral direction but also in the forward direction. The width b of the gripping jaw where it comes in contact with electrode plug ring 4 is chosen smaller than the width of electrode plug ring 4.

FIG. 7 shows schematically a clamp terminal 26, which has mounting tabs on its lower end.

Figure 3:
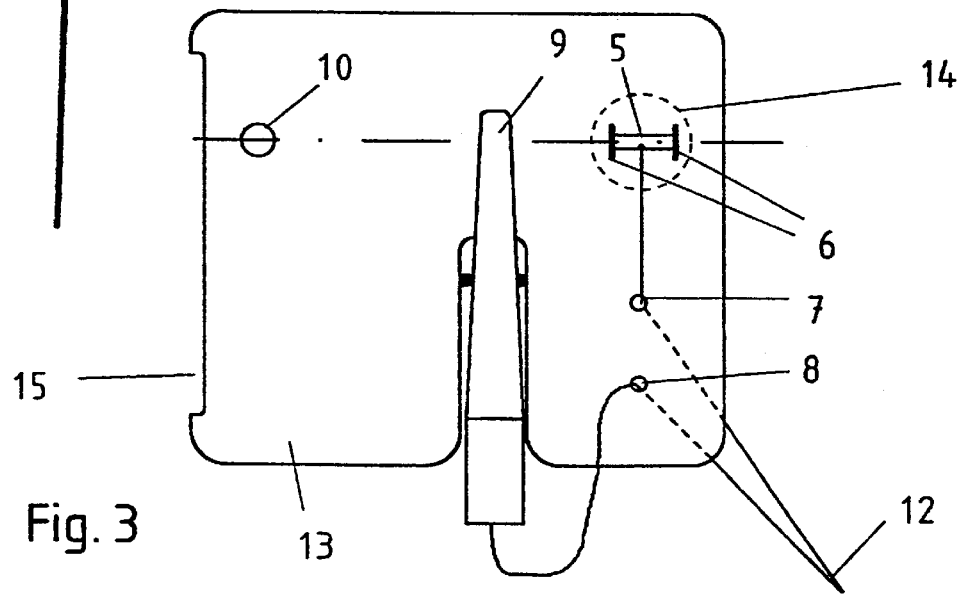
FIG. 3 shows the back view of the support element of FIG. 2.

In FIGS. 2 and 3, a cutout 15 in support element 13 can also be seen, which cutout serves to protect the wrapped-up wire 12 against slipping off during storage and shipping. Two slots 6 punched in support element 13 serve for the attachment of contact spring 5. The contact spring, as shown in the drawing, is held in the desired position by simply being pushed through the slots. Punched holes 7/8 serve to guide the wire strands and guarantee a certain tension relief.

Adhesive dot 14 over the solder joint that connects a wire strand to terminal spring 5 has the task of covering any sharp or pointed solder joints that may be present in order to prevent the OP gloves of the user from being damaged.

FIG. 5 shows the proximal end of the test cable, that is, the end lying in the nonsterile zone. Here again there is a proximal support element 16 made of paperboard, which contains holes 19 and 20 as well as slots 18. Holes 19 and 20 once again serve to fix the wire in place and relieve tension on it, while slots 18 serve for the attachment of soldering eyes 17, which are passed through them. Each of soldering eyes 17 is soldered to one wire strand and either has a cover made of an adhesive dot or is soldered on the bottom of soldering eye 17, so that any sharp parts that are present cannot occasion any damage. The soldering might be thought of in such a way that soldering eye 17 is first inserted into corresponding slot 18, the free end of soldering eye 17 is bent up perpendicularly, soldering is then done on the "bottom," and next the tab on the soldering eye is bent back. Hole 27, approximately 5 mm in size, serves to hold the proximal support plate in place with the aid of a so-called fabric clip.

A paperboard card 21 is connected to the twin-conductor wire and bears important safety information for use.

The herein disclosed disposable test cable assembly is intended for one time use as a sterile connection between a test instrument and an electrophysiological probe having an electrode plug which includes a contact pin and a plug ring. The test cable assembly includes a support element or panel 13, such as a paper board card, which has an elongated open gap 11 extending inwardly from one edge of the panel and terminating in a closed end in a central area of the panel which is just wide enough to permit insertion of an alligator clip 9. An elongated tubular contact element or spring 5 is inserted into a pair of parallel slots 6 in the support panel 13 which are spaced from one side of and forward of the gap 11. The slots extend in the same general direction as the gap 11. The slots 6 are positioned so that when the contact pin 3 of the electrode plug 1 is inserted into the tubular contact element 5, the plug ring 4 of the electrode plug 1 will be positioned ahead of and in alignment with the gap 11. In this installed position of the electrode plug 1, a jaw of the alligator clip 9 will electrically contact the plug ring 4 when the alligator clip 9 is inserted in the gap 11 with jaws open and then closed after insertion. The alligator clip 9 is substantially disposed within the confines of the support panel 13 when it is in gripping engagement with the plug ring 4 and the edges of the gap 11 laterally restrain the alligator clip 9 when it is installed in the gap 11.

What is claimed is:

1. A disposable test cable assembly for sterile use between a test instrument and an electrophysiological probe having an electrode plug which includes a contact pin and a plug ring, said assembly comprising:

a test cable having two wires extending between said cables proximal and distal ends, a long narrow alligator clip electrically connected to the distal end of one of said wires of said test cable, said alligator clip having a pair of elongated spring loaded manually openable jaws, a support panel having an elongated open gap extending inwardly from an open end at an edge of said panel and terminating in a closed end in a central area of said panel, said gap being just wide enough to permit insertion of said alligator clip therein, an elongated contact element mounted on said support panel in transverse relation to said gap, said contact element being spaced from and in laterally offset relation to one side of said gap, said contact element being electrically secured to a distal end of the other of said wires of said test cable and being adapted to releasably and electrically connect to said contact pin of said electrode plug, said jaws of said alligator clip being engagable with said plug ring when said contact pin is connected to said contact element and said alligator clip is inserted into said gap with said jaws open and then allowed to close to grippingly engage said plug ring, said alligator clip being substantially disposed within the confines of said support panel and laterally restrained by the edges of said gap when said alligator clip is in gripping engagement with said plug ring.

2. The disposable test cable assembly of claim 1 having a hole in said support panel in alignment with said elongated contact element and spaced from and in laterally offset relation to the other side of said gap, said hole being adapted to allow passage of said electrode plug therethrough when said contact pin is connected to said contact element.

3. The test cable assembly as set forth in claim 2 wherein said contact element includes a tubular part terminating a funnel shaped bell which facilitates axial insertion of said contact pin.

4. The test cable assembly as set forth in claim 3 wherein said tubular part of said contact element is longitudinally slotted.

5. The test cable assembly as set forth in claim 1 having a slot in said support panel laterally offset from said one side of said gap and extending in the elongated direction of said gap, said contact element being insertable into said slot.

6. The test cable assembly as set forth in claim 5 having an electrode hole in said support panel in laterally offset relation to said other side of gap and in alignment with said elongated contact element, said electrode hole being sufficiently large to permit said electrode plug to be passed through said electrode hole and connected to said contact element.

7. The test cable assembly as set forth in claim 1 wherein said support panel includes a cutout through which said other of said wires of said test cable passes in route to said contact element.

8. The test cable assembly as set forth in claim 1 wherein the connection between said other of said wires of said cable and said contact element is covered by an adhesive dot fixed to said support element.

9. The test cable assembly as set forth in claim 1 having a card shaped support for said proximal ends of said wires and wherein electrical contact elements are secured to said proximal ends of said wires and are mounted on said card shaped support.

10. The test cable assembly as set forth in claim 9 wherein said card shaped support has two pairs of parallel and mutually aligned slots and wherein said electrical contact elements are soldering eyes inserted respectively in said two pairs of slots.

11. The test cable assembly of claim 9 having a pair of openings in said card shaped support and wherein said wires pass respectively through said openings.

12. The test cable assembly of claim 1 wherein said support panel is made of paperboard.

13. The test cable assembly of claim 1 wherein said wires each include insulation whose outside diameter is not greater than 0.95 mm.

14. The test cable arrangement of claim 1 wherein said support panel has a quadrilateral shape.

* * * * *